(12) United States Patent
Hsu et al.

(10) Patent No.: US 8,203,013 B2
(45) Date of Patent: Jun. 19, 2012

(54) PREPARATION OF FATTY ACIDS IN SOLID FORM

(75) Inventors: Hsinhung John Hsu, Ventura, CA (US); Sergejs Trusovs, Ventura, CA (US); Tatjana Popova, Ventura, CA (US)

(73) Assignee: JH Biotech, Inc., Ventura, CA (US)

( * ) Notice: Subject to any disclaimer, the term of this patent is extended or adjusted under 35 U.S.C. 154(b) by 264 days.

(21) Appl. No.: 12/601,912

(22) PCT Filed: Aug. 28, 2008

(86) PCT No.: PCT/US2008/074572
§ 371 (c)(1),
(2), (4) Date: Nov. 25, 2009

(87) PCT Pub. No.: WO2009/032728
PCT Pub. Date: Mar. 12, 2009

(65) Prior Publication Data
US 2010/0179347 A1    Jul. 15, 2010

Related U.S. Application Data

(60) Provisional application No. 60/969,334, filed on Aug. 31, 2007.

(51) Int. Cl.
*C07C 51/00* (2006.01)
(52) U.S. Cl. .......... 554/156; 554/157; 562/513
(58) Field of Classification Search .......... 554/156, 554/157
See application file for complete search history.

(56) References Cited

U.S. PATENT DOCUMENTS

| | | |
|---|---|---|
| 5,191,097 A | 3/1993 | Dynes et al. |
| 5,380,893 A | 1/1995 | Lajoie |
| 5,434,279 A | 7/1995 | Wimmer |
| 6,998,496 B2 | 2/2006 | Luchini et al. |
| 7,098,352 B2 | 8/2006 | Strohmaier |
| 2007/0027343 A1 | 2/2007 | Duceppe et al. |

*Primary Examiner* — Deborah D Carr
(74) *Attorney, Agent, or Firm* — Ralph D. Chabot

(57) ABSTRACT

A method for making a fatty acid mineral salt is disclosed where liquid oils containing fatty acids are hydrolyzed using a base solution. A buffering agent is added to the hydrolyzed solution to maintain pH between 8.0 and 11.0 followed by a water soluble metal salt solution which causes a metathesis reaction with the hydrolyzed solution, forming a precipitates of fatty acid metal salts which are glycerin-free. The precipitates are filtered, washed and subsequently dried. The produced fatty acid metal salt is easier for the human body to digest than omega-3 fatty acid in oil form and also is less prone to oxidation and emitting of unpleasant odor.

19 Claims, No Drawings

PREPARATION OF FATTY ACIDS IN SOLID FORM

CROSS REFERENCE TO RELATED APPLICATIONS

This application claims the benefit of U.S. Provisional Application No. 60/969,334, filed Aug. 31, 2007, the content of which is hereby incorporated by reference herein in its entirety for all purposes.

FIELD OF THE INVENTION

The present invention relates to preparing fatty acids derived from fish and plant oils into a solid form capable of being digested by the human body.

BACKGROUND OF THE INVENTION

Interest in the omega-3 (as well as omega-6 and omega-9) fatty acids as health-promoting nutrients has expanded dramatically in recent years. A rapidly growing literature describes the benefits of polyunsaturated fatty acids in alleviating cardiovascular disease, atherosclerosis, autoimmune disorder, diabetes, and other diseases.

Extensive research indicates that omega-3 fatty acids reduce inflammation and help to prevent certain chronic diseases such as heart disease and arthritis. These essential fatty acids are highly concentrated in the brain and appear to be particularly important for cognitive and behavioral functions. In fact, infants who do not receive sufficient omega-3 fatty acids from their mothers during pregnancy risk improper vision and nerve development.

Omega-3 fatty acids are considered essential fatty acids, which are essential to human health but cannot be produced by the human body. For this reason, omega-3 fatty acids must be obtained from another source, primarily food.

Fish oils and plant oils are the primary dietary source of omega-3 fatty acids. Omega-3 fatty acids are found in cold-water fish such as salmon, mackerel, halibut, sardines, and herring. Omega-3 fatty acids are also found in flaxseeds, flaxseed oil, canola (rapeseed) oil, soybeans, soybean oil, pumpkin seeds, pumpkin seed oil, purslane, perilla seed oil, walnuts, and walnut oil. Also known as polyunsaturated fatty acids, omega-3 (and omega-6) fatty acids are beneficial to the human brain and the human body's normal growth and development.

Evolutionary assessments suggest that people in most western countries are consuming far less omega-3 fatty acids than now appears to be nutritionally desirable. Fish oils are the best sources of omega-3 fatty acids, but the consumption of fish is too low to meet the requirements. Efforts to supplement foods with omega-3 fatty acids have not been very successful because of the generally distasteful flavors and odors associated with the oils. The omega-3 rich fish oils are extremely susceptible to oxidation, thus requiring control of oxidation and off flavor development. Although antioxidants have been successfully added to fish oils to reduce the odor, a problem nevertheless remains particularly for individuals incapable of digesting omega-3 fatty acids in oil form as a result of ineffective enzyme production in the particular individual.

The extremely high sensitivity of omega-3 fatty acids to oxygen is related to: 1) molecular structure of the omega-3 acids; and, 2) liquid state of the fish oil containing omega-3 fatty acids. Some aspects of omega-3 oxidation are provided below for a better understanding of the disclosed method.

It is known to those skilled in the art that oxidation of organic compounds in the liquid phase (N. M. Emanuel, E. T. Denisov, Z. K. Maizus. Liquid Phase Oxidation of Hydrocarbons, Plenum Press, New York, 1967) consists of several consecutive steps. These steps are: (1) oxygen diffusion into the liquid phase; (2) initiation; (3) propagation; (4) branching; and, (5) termination.

Diffusion of oxygen (1) into the liquid is facilitated by the mixing of gas and liquid. The more intensively they are mixed, the faster oxygen saturation will be reached and the faster the oxidation reaction will occur. It is important to note that gas diffusion into solids is significantly slower than diffusion into liquids.

Chain initiation (2) during oxidation occurs as a result of the interaction between oxygen and the reaction center on the omega-3 molecule. The rate of initiation depends on the strength of C—H bond and on the stability of free radicals produced during the course of this type of reaction. Specific distribution of double bonds in omega-3 molecules makes these free radicals quite stable compared to other types of free radicals produced during the initiation reaction. Radicals produced as a result of the chain initiation reaction, reacts further with another oxygen molecule and is transformed into peroxy radical.

Chain propagation (3) is the reaction between a peroxy radical and another molecule of omega-3 fatty acid. A new free radical and hydroperoxide molecule are produced. It is important to mention that usually the chain propagation is a reaction between two separate molecules and its rate to a great extent depends on the velocity of molecular movement. The mobility of molecules in a liquid phase is high while mobility in a solid state is much slower. In a solid state, molecules do not move, but oscillate. This is why solid state chain propagation reaction rate is much slower.

Chain branching (4) occurs as a result of the split of hydroperoxides. In a liquid phase this reaction is the reason for the so-called self acceleration oxidation process. In a solid phase, this reaction is not significant because of the cell effect.

This leads to the conclusion that if omega-3 fatty acids can be converted and stored in a solid state with no any changes to its molecular structure, oxidative stability will increase.

Omega-3 fatty acids can also be made in capsule form with the primary constituent being either fish oil or flaxseed oil. It is known that all oils containing unsaturated fatty acids are very susceptible to oxidation by air oxygen and other oxidation agents. Oxidation of these oils causes dramatic and undesirable changes in their taste and aroma and tremendously decreases their nutritional value. This is the reason that these oils are recommended to be refrigerated.

Presently, the popular omega-3 fatty acids consumed by humans are provided in the form of oils. Following consumption, omega-3 oils (chemically -triglycerides of the omega-3 fatty acids) are hydrolyzed into free omega-3 fatty acids and glycerin by the actions of stomach and pancreatic juices. However, many people have difficulty digesting oils and fats, thus placing additional stress on the pancreas, liver and gallbladder.

The pancreas secretes pancreatic juice, which contains three enzymes that break down carbohydrates, fats, and proteins. The gallbladder secretes bile that helps dissolve fats. Digestive disorders are possible in some individuals because either the pancreas or gallbladder are unable to function properly. This ultimately may preclude a particular human body from consuming sufficient amounts of oils containing omega-3 fatty acids.

The prior art also discusses various methods for manufacturing salts (mainly, calcium salts) of unsaturated fatty acids.

These methods are based on the reaction of fats with calcium oxide in the presence of water at high temperature. U.S. Pat. No. 858,295 issued to Krebittz describes the preparation of soap and having the first production step preparation of calcium salt of fatty acid. U.S. Pat. No. 898,547 issued to Barrett, describes the manufacture of insoluble lime salts of fatty acids by reacting fatty matter with hydrate lime at 200° C. U.S. Pat. Nos. 6,229,031, 6,559,324, 6,576,667 issued to Strohmaier and U.S. Pat. No. 5,382,678 issued to Vinci describe the preparation of calcium salts from unsaturated fatty acids, including omega-3 acids.

All of the aforementioned patents described above teach a synthetic method based on reaction of the liquid oil with a stoichiometric excess of calcium oxide in the presence of water. As a result, these patented procedures produce a product containing calcium salts of fatty acids. These references disclose that the calcium salt product contains up to 5% unreacted oil and further contains glycerin that remains in the product. It is to be noted that calcium salt of omega-3 fatty acids made according to Strohmaier and Vinci have a very high pH due to the remaining unreacted calcium oxide present and as a consequence, cannot be used for human consumption. It is also important to note the patents described above do not provide, teach or suggest the possibility for the preparation of other than calcium salts of fatty acids.

Finally, all salts of omega-3 of fatty acids produced in accordance with the patents discussed above contain unhydrolized triglycerides, non-reacted calcium oxide or calcium hydroxide which provide little or no nutritional value to the salts produced.

SUMMARY OF THE INVENTION

The present invention relates to a process for the production of high purity glycerin-free fatty acids in a solid form of essential minerals which is more resistant to oxidation. The intention of the present invention is to prepare, from fatty acids found in fish oil or vegetable oil, a fatty acid metal salt which is more easily digested by humans and is more resistant to oxidation. The produced fatty acid metal salt does not contain glycerin or calcium oxide (hydroxide); compounds which are detrimental to the overall product produced.

Use of calcium hydroxide is undesirable because of its low solubility in water and formation of undesirable suspensions making it difficult to separate from the fatty acid mineral salt precipitate formed. Any glycerin present in the final product above a de minimus level is detrimental due to its tendency to increase the rate of oxidation.

The present disclosure provides for the delivery of beneficial omega-3 oils to the human body by the conversion into a solid form containing free omega-3 fatty acid salts. In this solid form, the product can exhibit substantially less odor than from a fatty acid oil source; will not suffer from excessive oxidation degradation; and is readily digestible.

The process begins with providing a source of fatty acids such as fish oils or vegetable oils.

Fish oils containing the omega-3 and/or omega-6 fatty acids are found in cold-water fish such as salmon, mackerel, halibut, sardines, and herring. For production purposes, fish oil is typically prepared in bulk and may contain oil from various species of fish. One such example is fish oil obtained in barrels from Jedwards International, inc., Quincy, Mass., USA. The content of the essential omega-3 fatty acids (as per certificate of analysis provided by the supplier) is 18% eicosapentaenoic acid (EPA) and 12% docosahexaenoic acid (DHA).

Besides fish oils, vegetable oils such as flaxseed oil, canola (rapeseed) oil, soybean oil, pumpkin seed oil, perilla seed oil, walnut oil, hemp seed oil, olive oil, coconut oil, and corn oil contain omega-3, omega-6, and omega-9 fatty acids and can be used.

Specifically described herein is a method for conversion of fatty acids, particularly omega-3 fatty acids from oils (esters of glycerin) into the form of metal salts of these acids. The produced mineral salts are buffered to be resistant to the detrimental effects (undesirable odor) of oxidation.

The solid form mineral or metal salts can be incorporated into a variety of food products providing essential omega-3 nutrition without exhibiting undesirable taste or aroma.

The metal salts of fatty acids formed according to our process can be formed using salts of essential metals selected from the group consisting of calcium, zinc, iron, magnesium, copper, manganese, chromium, etc., namely, calcium chloride, calcium bromide, calcium iodide, calcium nitrate, calcium acetate, magnesium chloride, magnesium bromide, magnesium iodide, magnesium nitrate, magnesium acetate, copper chloride, copper bromide, copper iodide, copper nitrate, copper sulfate, copper acetate, chromium chloride, chromium bromide, chromium iodide, chromium nitrate, chromium acetate, iron chloride, iron bromide, iron iodide, iron nitrate, iron sulfate, iron acetate, zinc chloride, zinc bromide, zinc iodide, zinc nitrate, zinc sulfate, zinc acetate, manganese chloride, manganese bromide, manganese iodide, manganese nitrate, manganese sulfate, manganese acetate, cobalt chloride, cobalt bromide, cobalt iodide, cobalt nitrate, cobalt sulfate, and cobalt acetate. However, calcium oxide and calcium hydroxide are specifically rejected as being part of our process because of their inability to become fully soluble as well as causing digestive problems for humans.

Because the product is a fatty acid metal salt, the product is also beneficial as a nutritional source of minerals.

During our process, the glycerin present in the oil molecule separated from the fatty acid molecule and is replaced by a metal. Glycerin is a substance having little or no nutritional or other beneficial value for human consumption. Glycerin is also detrimental because it is a liquid form, thus susceptible to oxidation and the production of undesirable flavor and odor.

Metal salts of fatty acids, being much more resistant to oxidation than the omega-3 fatty acids found in fish oils, still remain susceptible to oxidation particularly in alkaline conditions. However, alkaline environment oxidation can be remarkably decreased using our process.

A further goal of the present invention is to convert fatty acids, particularly omega-3 fatty acids, from its natural liquid state into metal salts which can be used more easily in a manufacturing environment for any number of products.

First, a fatty acid source such as either fish oil or vegetable oil are combined with an aqueous base solution to define a reactant mixture and, in the presence of an inert gas such as nitrogen, is stirred at a sufficient temperature for a sufficient time to substantially complete hydrolysis.

As a result of the stirring/heating and bubbling process, oils are hydrolyzed yielding glycerin and essential fatty acids in a form of acid salts.

Suitable bases include those oxides or hydroxides of alkali or alkaline earth metals that substantially fully solubilize in water. Preferably, these bases are selected from the group consisting of sodium hydroxide, potassium hydroxide, ammonium hydroxide, or combinations thereof.

Exact calculations of stoichiometry are impossible because of the indefinite molecular weight of fish oil. Additionally, supplies of fish oil may differ from one another because they may contain different species proportions, thus adding to the difficulty for calculating a precise molecular weight.

Fish oil chemically is a triglyceride having a large variety of fatty acids comprising its molecule. Literature suggests fatty acids in fish oil triglyceride molecules have from 14 to 24 carbon atoms or, from C14 to C24 polyunsaturated fatty acids. We make the assumption that fish oil fatty acids have an average length of carbon chains C18, and therefore estimate the molecular formula of the fish oil molecule to be $C_{57}H_{100}O_6$. The molecular weight of this "molecule" would calculate to be 880 g/mole.

Because the molecular weight of the fish oil fatty acids has been estimated, an excess amount of base is used to be certain the reactant mixture is driven to complete hydrolysis. This is necessary to ensure that substantially 100% of the glycerin capable of being formed is formed and is part of the intermediate solution.

The reactant mixture comprises: a) a fatty acid source containing esters of glycerin; b) a base of a sufficient quantity to separate all of the glycerin present from the fatty acid source; and, c) a sufficient quantity of water to solubilize the base. Preferably, the amount of base required is at least 3 moles of base for every mole of fatty acid source present. We have found through experimentation that at least a 2.0 Molar base solution would be sufficient; the quantity of solution to use would be dependent upon the quantity of the fatty acid source to hydrolyze. Below 2.0M, there becomes an insufficient amount of base present for efficient hydrolysis to occur.

The reactant mixture is initially a non-transparent emulsion which is stirred in the presence of an inert gas, preferably nitrogen, bubbling through and heated at a sufficient temperature and for a sufficient time to substantially complete hydrolysis.

Although room temperature may cause the reaction to occur, an elevated temperature is preferred, such as between 60-95° C. to increase the reaction rate. However, 100° C. is not recommended as this will cause undesirable foaming at atmospheric pressure. However, if a pressurized container is used for the reaction, 100° C. is possible.

In a preferred embodiment, the elevated temperature is between 90-95° C.

The stirring/heating/bubbling procedure is continued until the reactant mixture's physical appearance changes from a non-transparent emulsion into a colored transparent solution. This physical change is indicative of substantially complete hydrolysis. The reactant products comprise glycerin and fatty acids in the form of water soluble salts. It is to be noted that during the stirring/heating/bubbling procedure, volatile and semi-volatile substances originally present in the oil and that are responsible for emitting an unpleasant odor, are removed from the reactant mixture by the bubbling inert gas.

Next, after the hydrolysis procedure is complete, a buffering agent is added to maintain the pH of the solution. Buffering the solution to maintain a specific pH range is necessary to substantially reduce oxidation and create a stable, dryable precipitate of omega-3 fatty acid salts. While chemical structure of buffering agents(s) is known, the required amounts are established experimentally because the amount of buffering agent to use depends on the amount and type of reactants used.

Typical buffering agents may include organic and inorganic acids and their salts such as phosphoric acid, polyphosphoric acid, ascorbic acid, isoascorbic acid, malic acid, citric acid and their salts as well as ascorbic acid/potassium ascorbate, citric acid/potassium citrate, phosphoric acid/potassium phosphate, erythorbic acid/sodium erythorbate, and other combinations of organic and inorganic acids and their salts which can be used as well to maintain the desirable value of pH.

An aqueous salt solution containing an effective amount of metal is added to the buffered solution which causes a metathesis reaction and metal salt precipitates are formed. Preferably, the aqueous salt solution is selected from the group consisting of calcium chloride, magnesium chloride, zinc sulfate, iron sulfate, and manganese sulfate or combinations thereof.

The precipitate is thereafter filtered, washed and preferably vacuum dried and subsequently vacuum sealed in air-tight packaging. During this process, it is important that the pH not drop below the minimum desired level described in Table 1 for the aqueous salt solution used.

It has been discovered that the upper limit for pH is metal salt dependent. Table 1 indicates the recommended pH ranges for different aqueous salt solutions.

TABLE 1

| Aqueous salt solution | pH range |
| --- | --- |
| Calcium chloride | 8-11 |
| Zinc sulfate | 8-10 |
| Chromium chloride | 8-9.5 |
| Copper sulfate | 8-9.5 |
| Manganese sulfate | 8-9.5 |
| Iron sulfate | 8-10 |

In any case, every salt solution should maintain a pH of at least 8.0. Any lower and the precipitate formed may become undesirably viscous, sticky and prone to undesirable oxidation.

In a most preferred embodiment, anti-oxidants are added before the aqueous metal solution is added to the intermediate solution to help prevent oxidation of the fatty acid metal salt.

Although use of a synthetic anti-oxidant is possible, it is not preferred. This is because it will require a concentration in excess of the normally maximum use for food products of 200 ppm in order to effectively inhibit the oxidation of omega-3 fatty acids in solid state. Use of an essential oil as an anti-oxidant (discussed below) can be used in excess of 200 ppm and also has the additional benefit of providing a more pleasant smell, particularly to solutions derived from fish oils.

Essential oils for purposes of our invention include: Lavender, Tea tree, Eucalyptus, Bergamot, Cedarwood, Chamomile, Geranium, Ginger, Grapefruit, Helichrisum, Lemon, Lemongrass, Orange, Palmarosa, Citronella, Patchouli, Peppermint, Rosemary, Sandalwood, Wintergreen, etc. The choice of the essential oil that may be used to stabilize product protected from oxidation depends primarily on the formulator's taste.

Following precipitate formation, the precipitates are filtered, washed and dried. Drying can be performed by either at room or elevated temperature or more preferably, vacuum drying.

As a result of the method described above, the dried precipitate is a fatty acid metal salt having the appearance of a fine powder with high oxidative stability. The actual appearance and color of the fatty acid metal salt depends on the specific type of aqueous metal salt solution used.

BEST MODE FOR CARRYING OUT THE INVENTION

As stated earlier, the preferred method for obtaining a fatty acid metal salt is vacuum drying. However, because vacuum drying equipment was not available, the following test procedure was performed using a drying chamber and included the addition of an anti-oxidant.

EXAMPLE 1

Preparation of Calcium Salt of Omega-3 Fatty Acids

As stated earlier, the estimated molecular weight of a fish oil molecule is 880 g/mole. Using this molecular weight, the amount of base required can be calculated. In this example, potassium hydroxide (KOH) is used as the base.

One "mole" of fish oil is calculated to be 880 g and stoichiometrically requires 3 moles of KOH for a complete reaction, which is 56×3=168 g of solid KOH.

For complete fish oil hydrolysis to occur within a reasonable time period, the amount of base to use must be in excess of what is required stoichiometrically.

In this example, our test uses 50 g of fish oil and therefore 9.4 g of solid KOH is stoichiometrically required to be part of the base solution. However, we have found through experimentation that for complete fish oil hydrolysis to occur within a reasonable time period, the amount of KOH required to hydrolyze 50 g of fish oil is 15 g. Therefore, at least 1.57 (i.e. 4.7÷3) times the stoichiometrically calculated amount of base is required for substantially complete hydrolysis to occur.

A sufficient amount of water is required so that the amount of base used can be solubilized. An excessive amount of water is not desired because this can detrimentally slow down the reaction process.

In this example, 120 ml water and 15 g KOH, i.e. 2.2M solution of KOH, and 50 g of fish oil are placed into a flask and immersed into a boiling water bath, and the reactant solution is maintained at a temperature of approximately 90-95° C. The flask has a stirrer and tube reaching the bottom of the flask. The contents are stirred and nitrogen gas is bubbled through the tube into the reaction mixture for 6 hours until an intermediate solution is formed having a transparent yellow-brown appearance. The flask is removed from the heat and 0.5 g of ginger oil (essential oil) and 4.2 g of sodium erythorbate (buffer) are added to maintain the intermediate solution at a pH of 9.5 and stirred for 0.5 h.

Following the buffering stage, an aqueous salt solution is added. Based on stoichiometry, in order to precipitate the maximum amount of 3 moles of fatty acids which is capable of being produced from 1 mole of fish oil, 1.5 moles of a metal salt are necessary. In order to determine the amount of calcium chloride to use, 1.5 moles of calcium chloride per mole of fish oil is calculated to be 166.5 g (i.e., 111 g/mole×1.5 moles) of calcium chloride per 880 g of fish oil.

Through experimentation, in order to provide complete omega-3 fatty acids precipitation, approximately 15 g of dry calcium chloride per 50 g of fish oil. For complete precipitation to occur, the amount of calcium chloride required to precipitate 50 g of fish oil is 15 g or 2.4 moles is necessary. Therefore, at least 1.6 (i.e. 2.4÷1.5) times the stoichiometrically calculated amount of the active ingredient present in the aqueous salt solution was required for substantially complete precipitation.

Following addition of the buffering agent, it is not necessary for the intermediate solution to be further heated. The amount of calcium chloride added was 200 ml 0.7 M. White to off-white creamy precipitate is formed. The intermediate solution was stirred for 10-15 min. The precipitate was filtered and washed on the filter several times by water and then dried.

The final product obtained was 48 g of a fatty acid calcium salt having the appearance of white to off-white powder.

The same sequence was used to prepare fatty acid metal salts of other metal cations. The only difference was the amount of metal salt used as part of the aqueous metal salt solution (see Table 2) and the pH value maintained during the precipitation of omega-3 fatty acid salt of adequate metal (see Table 1). The desired amounts of metal salts used are established by the stoichiometric calculations. However, it should be noted that when metal cations are introduced into the intermediate solution, precipitates will form. Stoichiometric calculations are used to estimate the maximum yield of fatty acid metal salt.

TABLE 2

| Experiments | Metal salt | Salt Used, g | pH of process | Product yield g |
|---|---|---|---|---|
| 1 | Calcium chloride | 15 | 9.5 | 48 |
| 2 | Zinc sulfate | 27 | 9.2 | 57 |
| 3 | Chromium chloride | 24 | 8.0 | 55 |
| 4 | Copper sulfate | 38 | 8.6 | 58 |
| 5 | Manganese sulfate | 23 | 9.1 | 54 |
| 6 | Ferrous sulfate | 26 | 9.4 | 57 |

The effectiveness of the addition of anti-oxidants on odor reduction was also determined using fatty acid calcium salts by the method described in preceding Example 1.

Oxidative stability of the fatty acid metal salts produced was evaluated by measuring the amount of volatile organic compounds (VOC) in the sample. As mentioned earlier, the unpleasant smell of fish oil is derived from the VOC produced by oxidation. The amount of VOC present in the dried precipitate was quantified using EPA GC method 8015 that provides gas chromatographic conditions for the detection of the content of VOC in the sample.

The following results indicate that the fatty acid metal salt obtained using an anti-oxidant produces substantially less undesirable odor than standard fish oil.

Fatty acid calcium salt precipitates were produced in the presence of different buffering systems, approximately 48 grams each, and following filtration, were evenly distributed on an area of 7×7 inches and placed for air drying at room temperature. After 4 days of drying, the samples analyzed using EPA GC 8015 method.

The fatty acid calcium salt precipitates had different oxidative stability. Table 3 indicates that following 4 days of drying in open air at room temperature, fatty acid calcium salts had partially oxidized and emitted differing levels of VOC depending on the buffering system used.

TABLE 3

Volatile organic compounds content in omega-3 fatty acid calcium salts; After 4 days by EPA GC 8015 method

| No. | Buffering system | VOC, ppm |
|---|---|---|
| 1 | Phosphoric acid/potassium phosphate | 10,874 |
| 2 | Ascorbic acid/potassium ascorbate | 3,862 |
| 3 | Citric acid/potassium citrate | 4,226 |
| 4 | Sodium erythorbate | 3,037 |
| 4 | Sodium bisulfate | 13,463 |
| 5 | No buffering system | 19,897 |
| 6 | Fish oil alone | 48,000 |

VOC's present in the original fish oil is 27,000 ppm.

From the data presented in Table 3, fatty acid calcium salts emit a substantially lower level of VOC than fish oil exposed to open air at the same conditions. Conversion of fish oil into fatty acid calcium salts diminish the susceptibility of fatty acids to oxidation which in turn results in a reduced level of VOC emission. The most effective buffering systems with the highest antioxidant activity are ascorbic acid/potassium ascorbate and sodium erythorbate.

We claim:

1. A method for manufacturing a substantially glycerin-free fatty acid metal salt, not containing calcium hydroxide, comprising the following steps:
   combining:
   a) a fatty acid source containing glycerin esters and selected from the group consisting of: fish oil, flaxseed oil, canola oil, soybean oil, pumpkin seed oil, purslane, perilla seed oil, walnut oil, hemp seed oil, olive oil, coconut oil, corn oil or combinations thereof; and, b) at least a sufficient amount of a base for reacting with substantially all of said glycerin esters to form glycerin; and a sufficient amount of water to solubilize said base; said fatty acid source, base and water defining a reactant mixture;
   mixing said reactant mixture at a temperature of between 60-100° C. for a sufficient time and in the presence of an inert gas bubbling through to form an intermediate solution;
   adding a buffering agent to said intermediate solution to maintain the pH above at least 8.0; and,
   adding an aqueous metal salt solution to said intermediate solution whereby fatty acid metal salts are formed as precipitates.

2. The method of claim 1 further comprising the steps of filtering, washing, and drying said fatty acid metal salt precipitates.

3. The method of claim 1 where said base is selected from the group consisting of sodium hydroxide, potassium hydroxide, ammonium hydroxide or combinations thereof.

4. The method of claim 1 wherein said at least a sufficient amount of a base is at least 3.05 moles of base for every mole of said fatty acid source and the mixture of base with water is at a concentration of at least a 2.0 M.

5. The method of claim 2 wherein said at least a sufficient amount of a base is at least 3.05 moles of base for every mole of said fatty acid source and the mixture of base with water is at a concentration of at least a 2.0 M.

6. The method of claim 1 where said buffering agent is selected from the group consisting of: phosphoric acid, polyphosphoric acid, ascorbic acid, isoascorbic acid, malic acid, citric acid, and salts thereof, ascorbic acid/potassium ascorbate, citric acid/potassium citrate, phosphoric acid/potassium phosphate, erythorbic acid/sodium erythorbate, or combinations thereof.

7. The method of claim 1 where an anti-oxidant is added following formation of said intermediate solution and is selected from the group consisting of: lavender oil, tea tree oil, eucalyptus oil, bergamot oil, cedarwood oil, chamomile oil, geranium oil, ginger oil, grapefruit oil, helichrisum oil, lemon oil, lemongrass oil, orange oil, palmarosa oil, citronella oil, patchouli oil, peppermint oil, rosemary oil, sandalwood oil, wintergreen oil or combination thereof.

8. The method of claim 1 wherein said aqueous metal salt solution is selected from the group consisting of calcium chloride, calcium bromide, calcium iodide, calcium nitrate, calcium acetate, magnesium chloride, magnesium bromide, magnesium iodide, magnesium nitrate, magnesium acetate, copper chloride, copper bromide, copper iodide, copper nitrate, copper sulfate, copper acetate, chromium chloride, chromium bromide, chromium iodide, chromium nitrate, chromium acetate, iron chloride, iron bromide, iron iodide, iron nitrate, iron sulfate, iron acetate, zinc chloride, zinc bromide, zinc iodide, zinc nitrate, zinc sulfate, zinc acetate, manganese chloride, manganese bromide, manganese iodide, manganese nitrate, manganese sulfate, manganese acetate, cobalt chloride, cobalt bromide, cobalt iodide, cobalt nitrate, cobalt sulfate, cobalt acetate, or combinations thereof.

9. The method of claim 1 wherein said aqueous metal salt solution comprises at least 1.5 moles for every mole of said fatty acid source.

10. A method for manufacturing a fatty acid metal salt which comprises the following steps:
    combining: a) a fatty acid source selected from the group consisting of: fish oil, flaxseed oil, canola oil, soybean oil, pumpkin seed oil, purslane, perilla seed oil, walnut oil, hemp seed oil, olive oil, coconut oil, corn oil or combinations thereof; b) a base wherein the amount of base is such that there is at least 3.05 moles of base for every mole of said fatty acid source; and, c) a sufficient amount of water to solubilize said base and having a concentration of at least a 2.0 M; said fatty acid source, base and water defining a reactant mixture, said base selected from the group consisting of sodium hydroxide, potassium hydroxide, ammonium hydroxide, or combinations thereof;
    mixing said reactant mixture at a temperature of between 60-100° C. for a sufficient time and in the presence of an inert gas bubbling through to form an intermediate solution;
    adding a buffering agent to said intermediate solution to maintain the pH above at least 8.0;
    adding an aqueous metal salt solution to said intermediate solution whereby fatty acid metal salts are formed as precipitates; and,
    thereafter, filtering, washing, and drying said fatty acid metal salt precipitates.

11. The method of claim 10 where said buffering agent is selected from the group consisting of: phosphoric acid, polyphosphoric acid, ascorbic acid, isoascorbic acid, malic acid, citric acid, and salts thereof, ascorbic acid/potassium ascorbate, citric acid/potassium citrate, phosphoric acid/potassium phosphate, erythorbic acid/sodium erythorbate, or combinations thereof.

12. The method of claim 10 where an anti-oxidant is added following formation of said intermediate solution and is selected from the group consisting of: lavender oil, tea tree oil, eucalyptus oil, bergamot oil, cedarwood oil, chamomile oil, geranium oil, ginger oil, grapefruit oil, helichrisum oil, lemon oil, lemongrass oil, orange oil, palmarosa oil, citronella oil, patchouli oil, peppermint oil, rosemary oil, sandalwood oil, wintergreen oil or combination thereof.

13. The method of claim 10 wherein said aqueous metal salt solution is selected from the group consisting of calcium chloride, calcium bromide, calcium iodide, calcium nitrate, calcium acetate, magnesium chloride, magnesium bromide, magnesium iodide, magnesium nitrate, magnesium acetate, copper chloride, copper bromide, copper iodide, copper nitrate, copper sulfate, copper acetate, chromium chloride, chromium bromide, chromium iodide, chromium nitrate, chromium acetate, iron chloride, iron bromide, iron iodide, iron nitrate, iron sulfate, iron acetate, zinc chloride, zinc bromide, zinc iodide, zinc nitrate, zinc sulfate, zinc acetate, manganese chloride, manganese bromide, manganese iodide, manganese nitrate, manganese sulfate, manganese acetate, cobalt chloride, cobalt bromide, cobalt iodide, cobalt nitrate, cobalt sulfate, cobalt acetate, or combinations thereof.

14. The method of claim 10 wherein said aqueous metal salt solution comprises at least 1.5 moles for every mole of said fatty acid source.

15. A method for manufacturing a glycerin-free fatty acid metal salt that contains no calcium oxide and which comprises the following steps:

combining: a) fish oil containing a fatty acid; b) a base wherein the amount of base is such that there is at least 4.0 moles of base for every mole of fish oil; and, c) a sufficient amount of water to solubilize said base and having a concentration of at least 2.0 M; said fish oil, base and water defining a reactant mixture, said base selected from the group consisting of sodium hydroxide, potassium hydroxide, ammonium hydroxide, or combinations thereof;

mixing said reactant mixture at a temperature of between 90-95° C. for at least 5 hours in the presence of nitrogen gas bubbling through to change the physical appearance of said reactant mixture from a non-transparent emulsion to an transparent colored intermediate solution;

adding a sufficient quantity of buffering agent to said intermediate solution to maintain the pH above at least 8.0;

adding an aqueous metal salt solution to said intermediate solution to form precipitates of fatty acid metal salts; and, thereafter, filtering, washing, and drying said fatty acid metal salt precipitate.

16. The method of claim 15 where said buffering agent is selected from the group consisting of: phosphoric acid, polyphosphoric acid, ascorbic acid, isoascorbic acid, malic acid, citric acid, and salts thereof, ascorbic acid/potassium ascorbate, citric acid/potassium citrate, phosphoric acid/potassium phosphate, erythorbic acid/sodium erythorbate, or combinations thereof.

17. The method of claim 15 where an anti-oxidant is added following formation of said intermediate solution and is selected from the group consisting of:

lavender oil, tea tree oil, eucalyptus oil, bergamot oil, cedarwood oil, chamomile oil, geranium oil, ginger oil, grapefruit oil, helichrisum oil, lemon oil, lemongrass oil, orange oil, palmarosa oil, citronella oil, patchouli oil, peppermint oil, rosemary oil, sandalwood oil, wintergreen oil or combination thereof.

18. The method of claim 15 wherein said aqueous metal salt solution is selected from the group consisting of calcium chloride, calcium bromide, calcium iodide, calcium nitrate, calcium acetate, magnesium chloride, magnesium bromide, magnesium iodide, magnesium nitrate, magnesium acetate, copper chloride, copper bromide, copper iodide, copper nitrate, copper sulfate, copper acetate, chromium chloride, chromium bromide, chromium iodide, chromium nitrate, chromium acetate, iron chloride, iron bromide, iron iodide, iron nitrate, iron sulfate, iron acetate, zinc chloride, zinc bromide, zinc iodide, zinc nitrate, zinc sulfate, zinc acetate, manganese chloride, manganese bromide, manganese iodide, manganese nitrate, manganese sulfate, manganese acetate, cobalt chloride, cobalt bromide, cobalt iodide, cobalt nitrate, cobalt sulfate, cobalt acetate, or combinations thereof.

19. The method of claim 15 wherein said aqueous metal salt solution comprises at least 1.5 moles for every mole of said fish oil.

* * * * *